United States Patent [19]
Phillips

[11] Patent Number: 6,155,420
[45] Date of Patent: Dec. 5, 2000

[54] MEDICAL SYRINGE CONTAINER

[76] Inventor: Paul B. Phillips, P.O. Box 3510, Tampa, Fla. 33688-3510

[21] Appl. No.: 09/347,715

[22] Filed: Jul. 4, 1999

Related U.S. Application Data

[63] Continuation-in-part of application No. 08/820,636, Mar. 15, 1997, Pat. No. 5,918,443, which is a continuation-in-part of application No. 08/416,642, Apr. 5, 1995, Pat. No. 5,611,429.

[51] Int. Cl.<sup>7</sup> ..................................................... B65D 83/10
[52] U.S. Cl. ........................... 206/364; 604/192; 604/198
[58] Field of Search .................................. 206/364, 365; 604/192, 198

[56] References Cited

U.S. PATENT DOCUMENTS

| | | | |
|---|---|---|---|
| 3,008,570 | 11/1961 | Roehr et al. | 206/364 |
| 3,367,488 | 2/1968 | Hamilton | 206/364 |
| 3,434,587 | 3/1969 | Ciampa | 206/364 |
| 3,934,722 | 1/1976 | Goldberg | 206/365 |
| 4,278,437 | 7/1981 | Haggar | 604/198 |
| 4,300,678 | 11/1981 | Gyure et al. | 206/364 |
| 4,877,132 | 10/1989 | Makris et al. | 206/364 |
| 5,074,848 | 12/1991 | Burt et al. | 604/192 |
| 5,158,550 | 10/1992 | Scholl, Jr. | 604/192 |
| 5,161,681 | 11/1992 | Kemp et al. | 206/364 |
| 5,226,894 | 7/1993 | Haber et al. | 604/198 |
| 5,417,326 | 5/1995 | Winer | 604/192 |
| 5,718,334 | 2/1998 | Demel | 206/438 |

*Primary Examiner*—David T. Fidei
*Attorney, Agent, or Firm*—Charles A. McClure

[57] ABSTRACT

Telescoping leakproof two-piece medical syringe container. An upper tubular member or "cap" closed at its top end is wide enough along its vertical extent and downward to surround a syringe plunger, and also extends laterally from near its open lower end outward and downward to that end, so as to surround a finger grip of a syringe. A lower tubular member or "body" closed at its bottom end is wide enough along its vertical extent and upward to surround a syringe barrel with optional attached needle, and also extends laterally, from near its open upper end outward and upward to that end, so as to surround the syringe finger grip. The cap member and the body member telescope snugly together, and are retained against accidental opening by one or more detents on the open end of one of the tubular members overlapping the end of the other tubular member. At least one open end is tapered relative to the other open end to ensure that a leakproof container results when telescoped together.

8 Claims, 3 Drawing Sheets

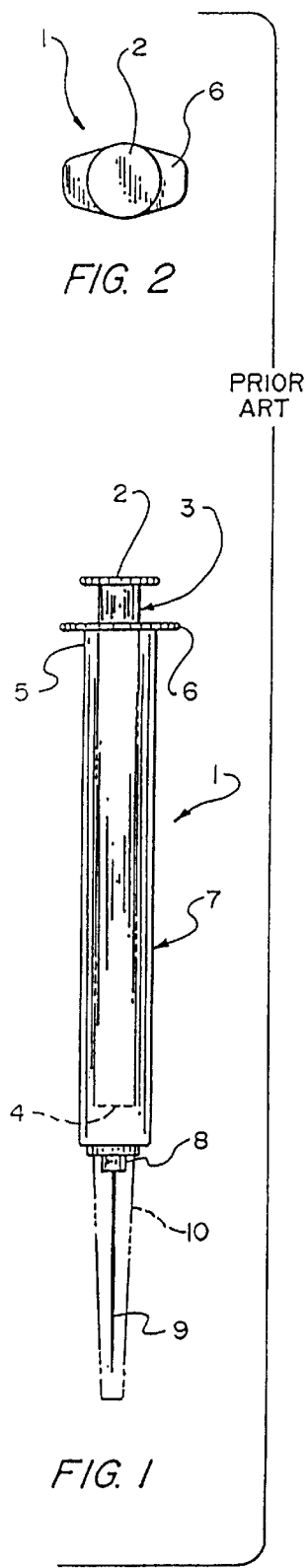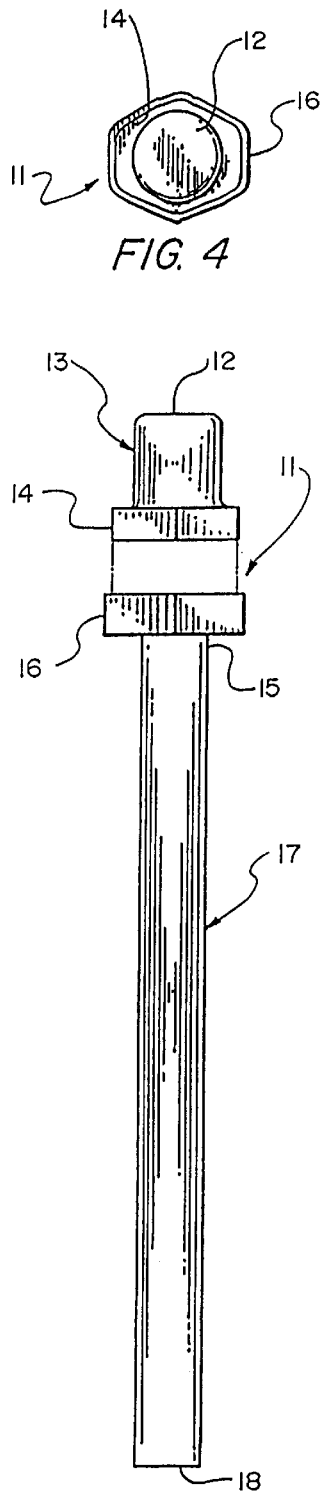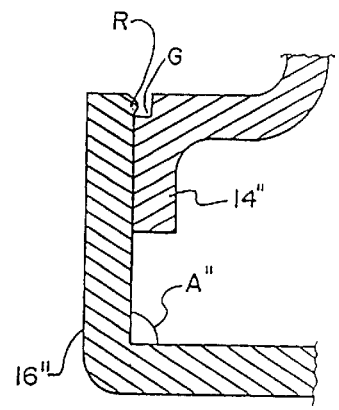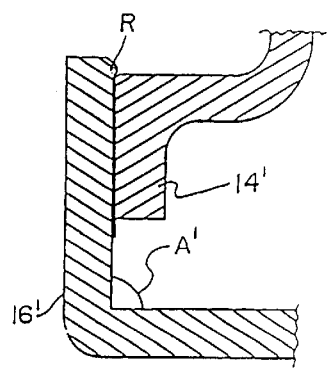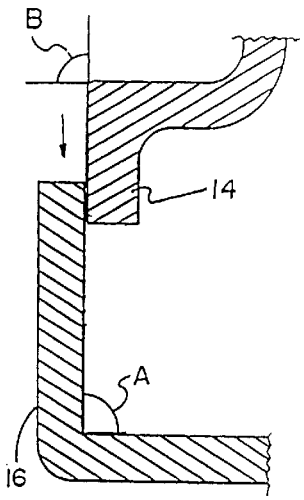

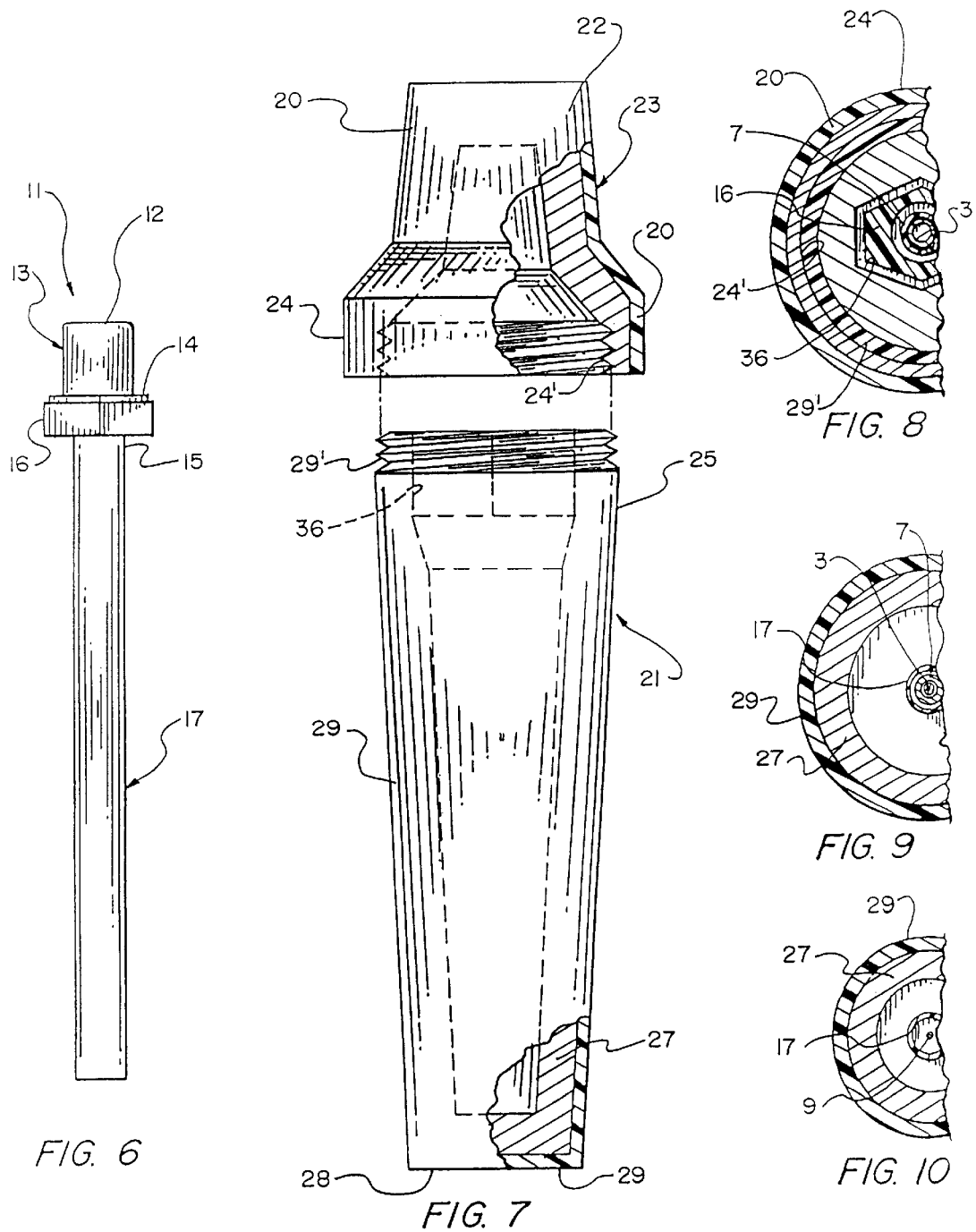

MEDICAL SYRINGE CONTAINER

This is a continuation-in-part of my allowed application Ser. No. 08/820,636, filed Mar. 15, 1997, now U.S. Pat. No. 5,918,443 as a continuation-in-part of my application 08/416,642 filed Apr. 5, 1995 issued as U.S. Pat. No. 5,611,429 on Mar. 18, 1997.

TECHNICAL FIELD

This invention relates to containment of medical syringes, and concerns especially their safe shipment for use and for disposal, especially such syringes with radiopharmaceutical contents/residues.

BACKGROUND OF THE INVENTION

Many or most medical syringes nowadays are intended for single use only, and for disposal promptly thereafter, to guard against the possibility of contaminating a subsequent patient or a health care professional with the blood of any patient or with any residual medication in the syringe. Where a medication comprises radioactive material, special care must be taken to prevent not only leakage of blood or medication liquid from the syringe but also exposure of the surroundings to radiation.

Collective disposal of used syringes with their needles (and other "sharps" such as scalpels and stitch cutters) is known, as in U.S. patents: to Haniff 4,657,139; and McCarthy 5,273,221. The trend toward one-time usage is conducive to immediate individual disposal, for which packages are known, as in Clanton 4,979,616 and in Yates et al. 5,293,616. Such one-syringe packages are bulkier than those for new syringes, as in Windischman 4,106,622 and in Cuu 4,634,428. Yet packaging of new syringes lacks provision for syringe disposal, so a new package is not convertible to a disposal package. Reich U.S. Pat. No. 5,519,931 teaches a two-part inner container useful within an outer two-part radiation-shielding container wherein (i) a filled syringe can be shipped along with the lower part (only) of the inner container, (ii) the used syringe can be reshipped after capping the inner container—which itself provides inadequate leak-resistance>.

Hence, a need exists for fluid leakproof disposal packages to hold individual filled and used syringes, and a related need exists for radiation shielding in the packaging of such syringes containing radiopharmaceutical medications and, after use, their residues. The present invention undertakes to meet these and related necessities.

SUMMARY OF THE INVENTION

A primary object of the present invention is to provide a fluid leakproof package for an individual medical syringe.

Another object of this invention is to accommodate, lengthwise in such package, a hypodermic syringe with a needle in place on it.

A further object of the invention is to accommodate, lengthwise. in such package, a plunger incompletely depressed into the barrel.

Yet another object of this invention is to provide a press-fit telescoping snap-lock leakproof structure for such package.

A still further object of the invention is to simplify the shipment of radiopharmaceutical compositions to a use location and from that location after use, shielding the surroundings from radiation.

In general, the objects of the present invention are attained by providing containers adapted to enclose a medical syringe, which may contain a radiopharmaceutical, sufficiently securely to seal off its contents, to protect the surroundings against fluid leakage therefrom, both when shipped (filled) to a place of use, and then when—with residual contents—likewise shipped to a disposal site. For radiopharmaceutical medicaments, an inner container leakproof to liquids and an outer container impervious to radiation are provided, such that the filled syringe can be enclosed in the inner container within the outer container, and the used syringe can be sent in the inner container replaced in the outer container to a disposal site.

A preferred embodiment of this first or inner container has a two-piece tubular structure providing a press-fit leakproof junction of the open ends of the component pieces assembled by juxtaposition.

Further, this fluid leakproof container is adapted to be used in combination with a surrounding radiation-shielding container, to protect the surroundings from radiation contamination therefrom, as whenever the filled syringe contains a radiopharmaceutical material. The press-fit fluid leakproof inner container fits for shipment: within the radiation-shielding outer container, which may have a twist-fit or equivalent closure.

Although reopenable manually under intentional extensive force, such inner container will not reopen or leak liquid contents under normal shipping or handling. Hence, it can protect the surroundings from possible leakage from a filled syringe before use, as shipped in filled condition, and from possible residue from a used syringes as when shipped to a disposal site. Radiopharmaceutical contents or residue are similarly secure and will not contaminate such an outer radiation-shielding container (or "pig") in its shipment either way.

Other objects of the present invention, together with means and methods for accomplishing the various objects, will be apparent from the following description and accompanying diagrams of a preferred embodiment being presented by way of example rather than limitation.

SUMMARY OF THE DRAWINGS

FIG. 1 is a side elevation of a conventional (prior art) disposable single-use medical syringe with attached needle, suitable for disposal according to this invention, as in subsequent views;

FIG. 2 is a plan view of the syringe of FIG. 1 (prior art);

FIG. 3 is an exploded side elevation of tubular components of a container of the present invention, open at adjacent ends but closed at opposite ends, to press-fit together around syringe and needle;

FIG. 4 is a plan view of the container components of FIG. 3;

FIG. 5A is a transverse sectional detail (enlarged) of corner features of a syringe container of this invention being assembled;

FIG. 5B is a transverse sectional detail (enlarged) of a second corner feature of a fully assembled container of this invention; and FIG. 5C is a transverse sectional detail (enlarged) of a corner feature partly similar to but partly different from that of FIG. 5B.

FIG. 6 is a side elevation of such a container, assembled from the components of FIG. 3, by press-fitting their open ends into fluid leakproof relationship about a syringe (and needle) of FIG. 1;

FIG. 7 is an exploded side elevation of components of another container (partly cut-away) useful along with the container of the preceding views according to this invention, having open adjacent ends (opposite ends closed) adapted, as by threading, to be twisted together and so assembled around the the medical syringe container;

FIG. 8 is a transverse sectional elevation through a composite container at the junction of the FIG. 7 components assembled around the FIG. 6 container with the syringe of FIG. 1 inside;

FIG. 9 is a similar transverse sectional elevation through the mid-part of a lower portion of the same composite container; and FIG. 10 is a similar transverse sectional elevation through an even lower part of the same resulting composite container.

DESCRIPTION OF THE EMBODIED INVENTION

Figure 11:
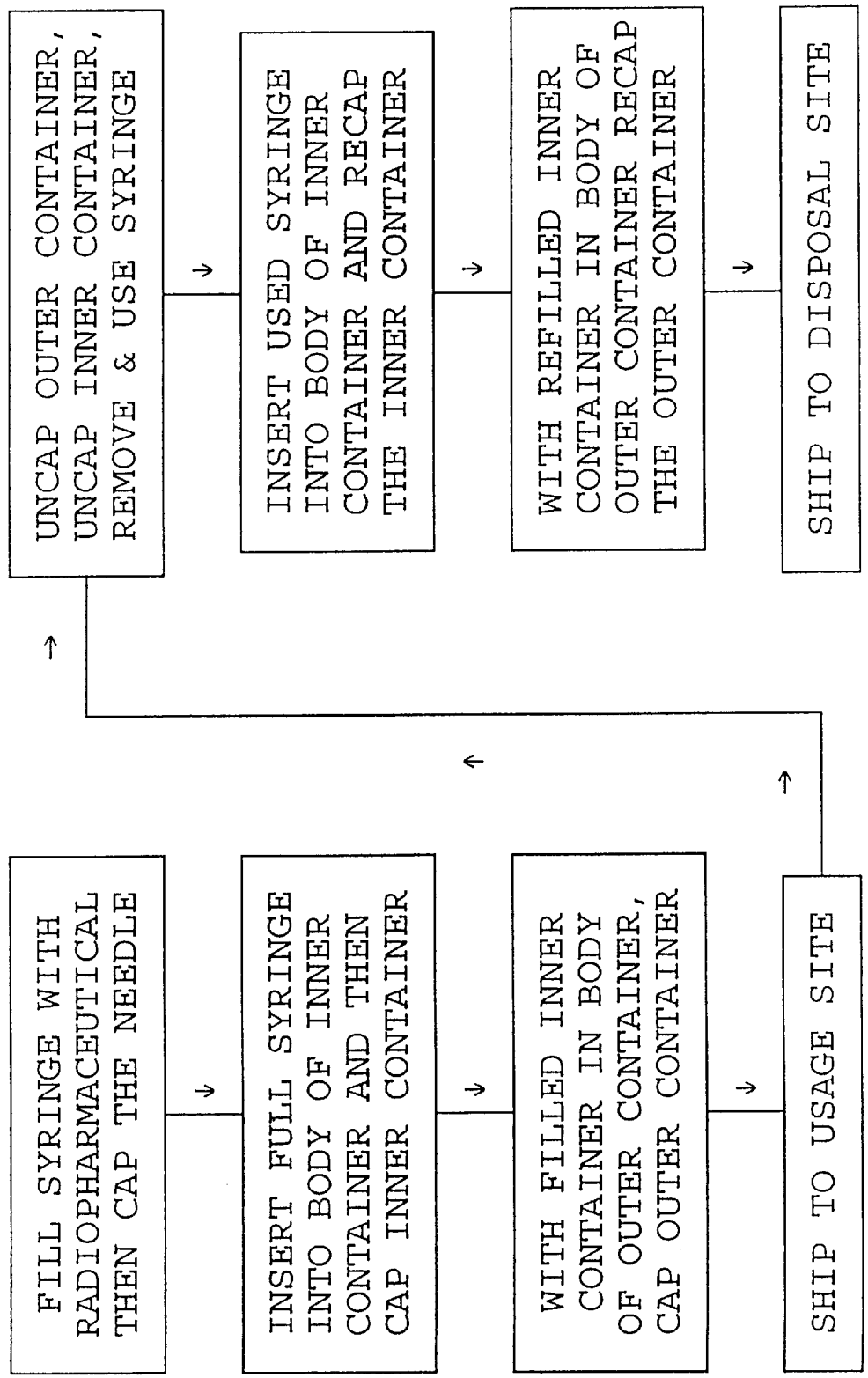
FIG. 11 is a block diagram showing various operation steps in practicing the method of this invention from beginning to end.

FIG. 1 shows, in side (or longitudinal) elevation, conventional (PRIOR ART) disposable single-use medical syringe 1, with attached needle 9, optionally surrounded by protective cover 10 (in phantom). The syringe itself has two main members: cylindrical barrel 7, and piston-like plunger 3 fitting slidably into the cylindrical barrel. The barrel is open at its plunger-receiving end 5, where it flares outward at opposite sides as finger-grip 6, and at its other end is constricted to tip 8 (open), where protective cover 10 encloses needle 9. The plunger is closed from its end 4 within the barrel and shown here nearly fully inserted, to its flared round (thumb-actuated) opposite exposed or top end 2.

A person holding such a conventional syringe can fill it wholly or partially with medicating liquid by manually withdrawing the plunger (partially) from the barrel with the (uncovered) needle end immersed in the liquid, and contrariwise can dispense the liquid from the syringe (after de-aerating it) via the needle by squeezing thumb and fingers to depress the plunger further into the barrel. A radiopharmaceutical should be given appropriate radiation-shielding. Hence, a syringe usually would be filled with a radiopharmaceutical by mechanical means rather than being filled manually. Any medical personnel manipulating such a syringe should be radiation-shielded.

FIG. 2 shows, in top plan, thumb-actuated end 2 of the syringe plunger, and finger-grip 6 (of the syringe barrel) protruding to the right and left sides. Otherwise both the plunger and the barrel are hidden behind or below that top end so are not visible in this view. The finger-grip hexagonal outline appears as elliptically elongated.

FIG. 3 shows, in exploded side elevation, two-piece embodiment of the syringe container of this invention, an "inner" container. Upper tubular container member or "cap" 13 has cylindrical upper portion 12 closed hatlike overhead, and has adjacent tubular brim portion 14 (hexagonal plan) open downward. Lower tubular container or "body" member 17 has, at upper end 15, similarly outlined portion 16 open cuplike upward and open axially downward to a long tubular housing portion terminating in closed bottom end 18. Open lower end portion 14 of cap 13 is so dimensioned to enable it to be press-fit: telescopically, contiguously, and snugly within upper end portion 16 of housing 17, thereby providing the respective tubular container members with a fluid leakproof junction.

FIG. 4 shows in plan, and FIG. 6 shows in side elevation, cap 13 and body 17 of container 11 as assembled. A generally hexagonal outline of the upper end portion 16 of the body closely surrounds slightly smaller similarly hexagonal lower end portion 14 of the cap 13, which also surrounds circular top 12 from this vantage point.

FIGS. 5A, 5B, and 5C show fragmentarily, in enlarged transverse section, and with wall thickness somewhat exaggerated, the corner detail(s) at a junction of open ends of both cap and body. Assembly of the container, as shown, depends upon telescoping of the close-fitting open lower end of the cap within the open upper end of the container body. Of course, if desired, the container parts could be resized from the illustrated inner/outer cap/body relationship to put the cap on the outside of the body, with like sealing effect, so long as the adjacent walls of cap and body become snugly contiguous, which provides the leakproof capability of the resulting container.

FIG. 5A shows downturned brim portion 14 of cap 13 entering (see arrow) the upper part of overlapping inner wall surface of cupped upper end portion 16 of body 17. It will be understood that the illustrated snugly contiguous relationship exists completely around the vertical axis of the cap and the body of this container. The downturned entering end is dimensioned to enter the upturned receiving end and to tighten therein, as both surfaces yield a bit until fully assembled. To assure leakproof contiguity of the wall surfaces while maintaining ready press-fit assembling of such open ends when they are juxtaposed, the entering end (here, the cap brim) may be tapered slightly inward (e.g., angle B as much as several degrees less than 90°) and/or the receiving end (here, the body top) may be tapered slightly outward (e.g., angle A as much as several degrees more than 90°). In fact, both angles might actually depart from a right angle in the same direction, so long as they differ at most about several degrees from one another in relative orientation.

FIGS. 5B and 5C show two arrangements of detent means effective to retain the assembled container in its fully assembled condition, as distinct from the leakproof characteristic—also present here. (Reference characters similar to those in FIG. 5A are single-primed in FIG. 5B, and double-primed in FIG. 5C, to denote alternatives.) Both embodiments are effective to keep the container securely closed once fully assembled. Yet it may be safely disassembled manually (pulled apart) by applying an extensive force to the respective end portions, just enough for them to flex or yield enough to restore the container to its separate original upper and lower members. Suitable polymeric compositions for the container are noted below.

FIG. 5B shows ridgelike detent R protruding from a portion of the inner edge of the cupped upturned end of top portion (here 16') of the body just above and overlapping the external shoulder corner of the downturned brim (here 14') of the cap. It will be understood that such overlapping secures the cap and housing together unless the resulting container is forcibly pulled apart, as by a person.

FIG. 5C is a similar view where the top body portion (here 16") engages complementary indentation or groove G optionally present in the corner of the brim shoulder portion (here 14") of the cap.

During assembly, a noticeable audible and tactile "snap" occurs as ridge R passes the brim corner, whether groove G is present there or not. Later disassembly whether unintentional or intentional, is deterred, although (as already indicated) remaining quite possible.

A detent (such as R)—and, when present, an indentation (such as G)—for receiving the detent-should occupy only a relatively minor part of the peripheral extent of the mating surfaces to enable convenient assembling (and disassembling) of this inner container. Preferably a pair of detents are used, one along the center third of each inside top edge of the furthest off-axial upturned narrow ends.

FIG. 6 shows in side elevation (reduced scale) fluid leakproof container 11 assembled from the FIG. 3 members by press-fitting the open end of cap 13 into fluid leak-proof relation, within the open end of body 17. The assembled container is understood here to be enclosing a syringe (and needle) of FIG. 1. Further enhanced protection may be obtained, as by enclosing container 11 as an inner container within an outer container, to form a composite container effective to shield the surroundings from radiation contamination as well as to preclude leakage of residual fluid.

FIG. 7 shows, in longitudinally exploded side elevation (on a like scale), a two-piece radiation-shielding container embodiment having cap 23 as its upper tubular member, and body 21 as its lower tubular member. Plastic outer skin layer 20 covers metallic (lead) radiation-shielding inner layer (uniformly shaded) The cap has sombrero-shaped top portion 22 opening downward within enlarged brim portion 24, whose metallic internal perimeter 24' is threaded.

Body 21 has plastic outer skin 29 including, at its open upper end 25, portion 29' externally threaded complementarily to the open internally threaded overlying cap. The metallic inner part of the body opens axially downward into long tubular portion 27, tapering to closed bottom end 28. When threaded together, the cap and body fit snugly and provide a radiation-shielding container—well adapted to holding an inner container shaped to accommodate the finger-grip portion of a syringe. As orienting the syringe finger-grip to fit into the hexagonal open end of the inner container assures secure assembly of that container, orienting the hexagonal outline of the inner container to fit into the receptive recess in the body of the outer container assures secure assembly of the outer container.

FIGS. 8, 9, and 10 show, in fragmentary transverse section at several levels, the composite container of this invention assembled on the outer (FIG. 7) container, enclosing the inner (FIG. 6) container, itself holding the FIG. 1 syringe (whether filled or used).

FIG. 8 shows through the outer container junction (from outside in) cap (23) skin layer 20, threaded inner wall 24', in mesh with threaded part 29' of body (21) skin layer 29. Recess 36 in body layer 27 of inner container (11) is hexagonal and accommodates similar horizontal portion 16 of the body of the inner container. The inner container is sectioned here just below the finger grip (not shown) of enclosed syringe barrel 7 and plunger 3 (both shown).

FIG. 9 shows a corresponding sequence of features through the mid-part of the same resulting composite container and its contents. Here the similarly directed sequence lacks the outer parts in FIG. 8 but shows skin 29 and body 27 of lower wall member 21 of the outer container, then the lower wall of inner container member 17, and finally cylindrical barrel 7 and plunger 3 of the syringe.

FIG. 10 resembles FIG. 9 at smaller diameter, and with needle 9 substituted for the syringe elements now above the plane of view.

FIG. 11 is a block diagram of the nature and the order of steps preferred according to the present invention. It renders operational aspects of this invention even more apparent-given the specified inner and outer containers or their equivalent (s). Preliminarily essential (at top of leftmost of two columns) is FILL SYRINGE WITH RADIOPHARMACEUTICAL THEN CAP THE NEEDLE, as medicament customarily is drawn in through the immersed needle by withdrawing the plunger far enough to fill the syringe with the intended quantity thereof. Next INSERT FULL SYRINGE INTO BODY OF INNER CONTAINER AND THEN CAP INNER CONTAINER. A syringe filled with a non-radioactive medicament could be shipped in the so-called "inner" container, alone or with others suitably wrapped, but when filled with a radiopharmaceutical, syringes are shipped individually and in a radiation-shielding (here called simply "outer") container. The final pre-shipment step is WITH FILLED INNER CONTAINER IN BODY OF OUTER CONTAINER, CAP OUTER CONTAINER. Then SHIP TO USAGE SITE as indicated by arrows leading to the top of the rightmost or second of the block diagram columns.

According to FIG. 11, the first block at the usage site reads UNCAP OUTER CONTAINER, UNCAP INNER CONTAINER, REMOVE & USE SYRINGE. Of course, a syringe containing a radiopharmaceutical is manipulated with special care in use. Similarly, its disposal demands special handling and shipment, as the used syringe may properly contain a radioactive residue. Hence, INSERT USED SYRINGE INTO BODY OF INNER. CONTAINER AND RECAP THE INNER CONTAINER rendering it leakproof here. As the inner container body may have been left in the outer container body, or may have been removed preparatory to syringe usage, the next block reads WITH REFILLED INNER CONTAINER IN BODY OR OUTER CONTAINER RECAP THE OUTER CONTAINER. Finally SHIP TO DISPOSAL SITE, where proper steps can be taken to recover whatever is re-usable and to destroy or reprocess appropriately whatever is recoverable.

No unusual materials of construction are required. The syringe may be made of organic polymeric material (plastic) or even glass, or the plunger may be made of one such composition, and the barrel be made of another such composition. The syringe inner container may be made of polyalkylene, polycarbonate, or like composition from the textile and plastic film arts. The outer container's ability to shield the surroundings from radiation contamination is a function of mass, so it is preferably mainly lead, and thick enough to meet radiation health and safety standards, usually covered by plastic.

Instead of threaded turns as in the illustrated embodiment of outer container, an equivalent twist-fit junction (not shown) may have one member's transverse end surface vertically slotted and ramped to admit two or more evenly spaced balls on respective stems extending from the opposite member's like end surface, enabling the ends to be drawn together with a simple partial turn.

Advantages and benefits of practicing the present invention in its various aspects have been stated above and doubtless will become most apparent to those persons who actually undertake its practice. Included should be the following, (i) a leakproof inner container, (ii) with a snap-lock closure precluding accidental reopening but enabling safe handling and intentional manual reopening, (iii) a radiation-shielding outer container receptive to the inner container properly assembled, (iv) shippable to and (v) manually reopenable at a use location; and, after usage to dispense contained medicament, (iv) the syringe is readily replaceable in the still leakproof inner At. container, (v) which is readily replaceable in the outer container, for (vi) safe shipment to a disposal/reclamation site, where (vii) the outer container may be reclaimed and the rest including residual blood or other bodily fluids be appropriately destroyed or otherwise disposed of according to accepted safe practices.

Other benefits are uniform and systematic handling of new, or filled, and later used medical syringes, and the resulting savings, not least a reduction in costs of dealing with (or insuring against) possible economic consequences of personal encounters with harmful syringes and their residues through negligent handling or otherwise.

Preferred embodiments and variants have been suggested for this invention. Other modifications may be made, as by adding, combining, deleting, or subdividing compositions, parts, or steps, while retaining all or some of the advantages and benefits of the present invention—which itself is defined in the following claims.

The claimed invention:

1. Leakproof container, for enclosing a syringe having an upright plunger fitting slidably down into the open upper end of a barrel provided with a lateral finger grip portion and extending downward to a needle junction with optional attached needle; comprising an upper tubular cap member closed at its top end, open at its bottom end, and wide enough along its vertical extent and downward to surround a syringe plunger, and also extending further laterally from near its open bottom end outward and downward to that end, so as to surround the syringe finger grip, and further adapted to telescope snugly against a complementary tubular member;

a complementary lower tubular body member closed at its bottom end, open at its top end, and wide enough along its vertical extent and upward to surround a syringe barrel and attached needle, and also extending laterally, from near its open top end outward and upward to that end, so as to surround the syringe finger grip, and further adapted to telescope snugly against the cap member;

the respective members forming a leakproof seal when assembled by press-fit telescoping of their respective open ends together;

wherein both tubular members are circular in cross-section except at their open ends, where they are widened along a transverse axis to fit around the syringe finger grip and to enable the respective tubular members to be press-fit completely together and to deter re-opening, while enabling re-opening by forceful manipulation to pull them apart.

2. Container according to claim 1, wherein the open end cross-sections are generally hexagonal with elliptical symmetry.

3. In a two-piece container having an upper tubular cap member open at its lower end and a lower tubular body member open at its upper end, the respective open ends being juxtaposable for enclosing a syringe having an upright plunger fitting slidably down into the open end of a syringe barrel provided with a lateral finger grip portion and extending downward to a needle junction;

the improvement wherein the upper tubular cap member is laterally wide enough along its vertical extent so as to surround a syringe plunger, and is enlarged laterally along its open lower end to accommodate the lateral extent of such a syringe finger grip; and the lower tubular body member is laterally wide enough along its vertical extent so as to closely surround a syringe barrel, and is enlarged laterally along its open upper end to accommodate the lateral extent of the syringe finger grip;

the open ends of the respective tubular members being adapted to telescope snugly together about such a syringe finger grip;

wherein the tubular cap and body members are substantially circular in transverse section except at their laterally extending finger-grip-accommodating ends.

4. Container according to claim 3, wherein the telescoping ends are substantially hexagonal in transverse cross-section.

5. Telescoping two-part container for medical syringes, comprising a tubular upper cap member closed at its top end but open at its lower end, being enlarged laterally outward into an upright shoulder portion at its junction with the rest of this member;

a tubular lower body member closed at its bottom end but open at its upper end, being enlarged laterally outward into an inverted shoulder portion at its junction with the rest of this member;

the open end portions of the respective members being similar in cross-section, and being sufficiently large to fit about the finger-grip of a conventional medical syringe;

the respective members being adapted to be assembled by being press-fit together telescopically, one end within the other end;

the open end portion of at least one such member tapering relative to the open end portion of the other such member, whereby the respective end portions tighten against one another during such assembly, as the extent of their overlapping increases;

the open edge of such overlapping member having a detent adapted to engage the shoulder of such overlapped member when the two are fully assembled, thereby deterring accidental disassembly of the container, without precluding their intentional disassembly.

6. Medical syringe container according to claim 5, whereby the resulting assembled container is leakproof in intended use.

7. Medical syringe container according to claim 5, wherein the open end portions of the respective members are enlarged in a generally elliptical outline throughout a pair of radially opposite arcuate portions of their respective cross-sections, and so adapted to fit snugly about a conventional medical syringe finger-grip.

8. Medical syringe container according to claim 7, wherein the generally elliptical plan outline of the respective open end portions is in the form of a laterally elongated hexagon.

* * * * *